United States Patent
Sakunenko et al.

(10) Patent No.: US 10,168,293 B2
(45) Date of Patent: Jan. 1, 2019

(54) FLUIDS LEAKAGE SENSOR

(71) Applicant: InventionXT LLC, Dallas, TX (US)

(72) Inventors: Iurii Sakunenko, Moscow (RU);
Vladimir Kondratenko, Moscow (RU)

(73) Assignee: InventionXT LLC, Dallas, TX (US)

( * ) Notice: Subject to any disclaimer, the term of this patent is extended or adjusted under 35 U.S.C. 154(b) by 3 days.

(21) Appl. No.: 15/442,116

(22) Filed: Feb. 24, 2017

(65) Prior Publication Data
US 2018/0246048 A1    Aug. 30, 2018

(51) Int. Cl.
| | | |
|---|---|---|
| *G01R 27/02* | (2006.01) | |
| *G01R 27/08* | (2006.01) | |
| *G01R 27/22* | (2006.01) | |
| *G01R 31/02* | (2006.01) | |
| *G01R 31/08* | (2006.01) | |
| *G01R 31/11* | (2006.01) | |
| *G01N 27/04* | (2006.01) | |
| *G01N 27/07* | (2006.01) | |
| *G01M 3/16* | (2006.01) | |
| *G01M 3/40* | (2006.01) | |
| *H01R 43/00* | (2006.01) | |
| *H01B 7/32* | (2006.01) | |
| *G01N 27/416* | (2006.01) | |

(52) U.S. Cl.
CPC ............ *G01N 27/048* (2013.01); *G01M 3/40* (2013.01); *G01N 27/416* (2013.01)

(58) Field of Classification Search
CPC ........ G01R 27/08; G01R 27/22; G01R 31/08; G01R 31/11; G01R 31/02; G01R 27/02; G01N 27/04; G01N 27/07; G01M 3/16; G01M 3/40; H01R 43/00; H01B 7/32; H01B 7/34
See application file for complete search history.

(56) References Cited

U.S. PATENT DOCUMENTS

| | | | | | |
|---|---|---|---|---|---|
| 4,594,638 | A | * | 6/1986 | Suzuki .................. | G01M 3/165 174/11 R |
| 4,710,353 | A | * | 12/1987 | Tanaka .................. | G01M 3/165 385/12 |

(Continued)

FOREIGN PATENT DOCUMENTS

| | | |
|---|---|---|
| JP | 08271461 A | 10/1996 |
| JP | 3699708 B2 | 9/2005 |

(Continued)

*Primary Examiner* — Jermele M Hollington
*Assistant Examiner* — Neel Shah
(74) *Attorney, Agent, or Firm* — Vinson & Elkins LLP

(57) ABSTRACT

The present disclosures relates to a leakage sensor cable comprising a first conductive wire and a second conductive wire; a first conductive coating layer formed around the first conductive wire; a second conductive coating layer formed around the second conductive wire; a first permeable shell formed around the first conductive coating layer to form a first sensor cord; a second permeable shell formed around the second conductive coating layer to form a second sensor cord; wherein the first sensor cord and the second sensor cord are arranged together along their lengths to form a leakage sensor cable; and wherein the permeable shell is impregnated with electrolyte particles. The leakage sensor can be combined with a resistance-meter connected to the leakage sensor cable to form a leakage sensor assembly.

9 Claims, 3 Drawing Sheets

(56) References Cited

U.S. PATENT DOCUMENTS

| | | | | |
|---|---|---|---|---|
| 4,783,576 A | * | 11/1988 | Silver | H01B 9/0605 |
| | | | | 156/53 |
| 4,862,146 A | * | 8/1989 | McCoy | G01M 3/04 |
| | | | | 174/11 R |
| 5,355,720 A | * | 10/1994 | Bailey | G01M 3/165 |
| | | | | 324/533 |
| 7,081,759 B2 | * | 7/2006 | Raymond | G01M 3/165 |
| | | | | 324/539 |
| 8,256,269 B2 | | 9/2012 | Raymond | |
| 8,601,679 B2 | | 12/2013 | Raymond | |
| 2010/0211226 A1 | * | 8/2010 | Dowling | G05D 9/12 |
| | | | | 700/281 |
| 2014/0210603 A1 | * | 7/2014 | Walser | G01R 27/02 |
| | | | | 340/438 |

FOREIGN PATENT DOCUMENTS

| | | | |
|---|---|---|---|
| JP | 2013200220 A | 10/2013 | |
| KR | 101592099 A | 12/2015 | |
| RU | 25222 U1 | 9/2002 | |
| RU | 2312954 C1 | 12/2007 | |
| RU | 99156 U1 | 11/2010 | |
| RU | 2545485 C1 | 4/2015 | |

* cited by examiner

FLUIDS LEAKAGE SENSOR

BACKGROUND

The present disclosure relates to devices in the field of measurement equipment, in particular to indicating, recording and signaling devices actuated by electrical means. The device may be used as a sensor for detecting the leakage of water or other conductive fluids regardless of whether they are in a liquid state or whether they are able to conduct electricity.

Water and other fluids delivered through pipes held in reservoirs and containers play an important role in human society. When water is flowing in the manner intended and stays within its designated containers, water does great things for human civilization and modern life. But when water leaks from designated containers and delivery devices such as pipelines, it is a force for destruction. Most destructive and problematic in modern commercial and residential buildings is when water leaks from pipelines. The nature of these leaks makes them difficult to detect. Without adequate leak detection there cannot be a proper remedy. The effect of a small leak cumulated over time often results in significant damage that could have been mitigated if the leak had been detected earlier. The most troublesome of leaks occur in spaces and surfaces that are not typically accessible or open to monitoring. An example is the network of pipelines behind dry-wall or concrete walls of commercial and residential buildings. The point of leakage can be anywhere within the system and there is a significant amount of surface area that must be covered. Furthermore, the location or position at which a leakage sensor can be mounted significantly constrains the device. For example, for a horizontally placed pipeline, the leakage is likely only to be detectable at the bottom of the pipeline and as such it must be mountable upside-down on the bottom of the pipeline.

Another problem in water leakage detection is that the water is not always in a liquid state. In certain environments, the water is in a non-liquid or gaseous state such as water vapor or steam. Yet in other environments, the water leakage can occur in the form of water in mixed states—i.e., where the water can manifest as a liquid or as steam.

Yet another problem in water leakage detection is that water is not always able to conduct electricity. Water in certain environments (e.g. water used for cooling in data centers) is chemically clean and fully deionized. Where the water is purified to 99.99999991% degree of purification, the electrical resistance of water can be increased up to 18 mega-ohms-cm, making the water non-conductive.

Therefore, there is a need for a device capable of the sensitive detection of the leakage of water and fluids in various states and in various degrees of conductivity mountable on many types of locations and surfaces.

An example of an attempt at designing such a device is disclosed in Russian Patent No. RU 2312954 [C1, E03C 1/00, F24D 19/10, Dec. 20, 2007]. This device comprises a horizontal perforated plate, a water level sensor, a siphon and a tank with an open top where the dimensions of the tank's horizontal section is smaller than the dimensions of the perforated plate. The tank is attached underneath the perforated plate and is shifted to the edge. The tank has a hole at its bottom. The water sensor and the siphon are placed inside the tank such that the siphon's fold is located above the water level sensor. The holes on the perforated plate are positioned in such a way that at least one of them is located above the tank. The perforated plate has ribs that are arranged on the top part of the perforated plate, which forms a closed contour surrounding all the holes, except for those located above the tank, or the groove forming a closed contour surrounding all the holes except for those that are located above the tank, and on one hole the groove closes. The disadvantage of this device is its relatively narrow functionality, which in turn restricts its application for lengthy objects such as pipelines.

Another example of an attempt at designing such a device is disclosed in Russian Patent No. RU 25222 [U1, G01M 3/10, G01M 3/26, Sep. 20, 2002]. This device comprises a tank and a sensitive element posted therein, which is made in the form of a rod on which the following elements are mounted: a high-precision ultrasonic detector of a product level fluctuation, temperature gauges, a bottom water level sensor and an electronic unit connected to a computer that provides a software computation of interdependency of fluid temperature layers and the fluid level. The disadvantage of this device is its relatively narrow functionality, as it is designed for leak detection from reservoirs, and its application for extended objects, e.g. pipelines, is functionally restricted.

Another example of an attempt at designing such a device is disclosed in Russian Patent No. RU 99156 [U1, G01M 3/10, G01M 3/26, Nov. 10, 2010]. This device is an automatic electronic water sensor. It comprises a protective tube with a center pad made of intrinsically safe metal with built-in end electrodes hardwired to an electronic indicator. The electronic indicator contains an electronic circuit, a LED, and a buzzer connected to a power supply source and is dash-mounted. The disadvantage of this device is its relatively narrow functionality, as it is designed to indicate the presence of water in the tank without the ability to detect the location of the water leakage, which in turn restricts its application for lengthy objects such as pipelines.

Yet another example of an attempt at designing such a device is disclosed in Russian Patent No. 2545485 [C1, G01F23/18, Apr. 10, 2015]. This device includes two conductors, each in the form of at least one conductive wire, connected to an electronic indicator, wherein the electronic indicator is designed as a resistance meter. Each conductor is placed in a conductive coating made of a conducting polymer compound. A single water-permeable shell made of a capillary-porous material is located between and around the conductive coatings. One feature of this device includes that of a conductive polymer compound used for the conductive coating, which may be based on polyolefin and carbon soot in the ratio from 4:1 to 1:3. Another feature is the use of a twisted fiber glass filament or fiberglass roving that can be used as the water-permeable shell made of a capillary-porous material. The conductive coating made of a conductive polymer compound is designed to have a surface resistance Rs in the range of 1 to 103 Ohm. During manufacturing, it is possible to select various different compositions of the conductive polymer compound, as long as the surface resistance of the conductive coating layer achieves a surface resistance value between the range of 1 to 103 Ohm; the water-permeable shell made of a capillary-porous material is either in the form of a complete extended structure or in the form of a harness of a capillary-porous fiber wound around the conductors, which are placed in the conductive coatings made of a conductive polymer compound with a path in the form of closed eights. The disadvantage of this device is its low sensitivity, which is due, in part, to the relatively small size of the extended area of the water permeable shell made of a capillary-porous material. More-over, this device is incapable of detecting deionized water, making it useless in environments where deionized water is being delivered.

SUMMARY

The present disclosure relates to a leakage sensor cable comprising a first conductive wire and a second conductive wire; a first conductive coating layer formed around the first conductive wire; a second conductive coating layer formed around the second conductive wire; a first permeable shell formed around the first conductive coating layer to form a first sensor cord; a second permeable shell formed around the second conductive coating layer to form a second sensor cord. The first sensor cord and the second sensor cord may be braided together along their lengths to form a leakage sensor cable. The permeable shell may also be impregnated with electrolyte particles.

The electrolyte particles can be a salt. The permeable shell may also be made of a capillary porous material such as a twisted fiber glass filament or fiberglass roving. The conductive coating layer may be made of a conductive polymer compound comprised of polyolefin and carbon soot in a ratio of 4:1 to a ratio of 1:3.

A plurality of taps made of a capillary porous material extending away from the sensor cable can be attached. In one embodiment of the leakage sensor cable, a plurality of impermeable inserts can be formed around the first conductive coating layer and the second conductive coating layer immediately adjacent to the first permeable shell and second permeable shell. In another embodiment of the leakage sensor cable, a fastening thread may be coiled around the leakage sensor cable. The fastening thread may be made of a non-conductive material. In yet another embodiment of the leakage sensor cable, the impermeable layer can be configured to form a single water impermeable section or a plurality of water impermeable sections.

The leakage sensor can be combined with a resistance-meter connected to the leakage sensor cable to form a leakage sensor assembly.

A fluid can be detected by forming a first conductive coating layer around a first conductive wire. A first permeable shell is then formed around the first conductive coating layer to create a first sensor cord. A second conductive coating layer is formed around a second conductive wire. A second permeable shell is then formed around the second conductive coating layer to create a second sensor cord. The first sensor cord and the second sensor cord are arranged together to form a leakage sensor cable. When a conductive fluid enters the first permeable shell and the second permeable shell, an electrical current is then conducted from the first conductive wire to the second conductive wire through the conductive fluid.

Also, the first permeable shell and the second permeable shell may be impregnated with electrolyte particles. When a fluid (whether conductive or non-conductive/deionized) enters the first permeable shell and the second permeable shell, the conductivity of the fluid is enhanced by dissolving the electrolyte particles into the fluid. An electrical current is then conducted from the first conductive wire to the second conductive wire through the conductive fluid.

BRIEF DESCRIPTION OF THE DRAWINGS

These and other features, aspects, and advantages of the present disclosure are illustrated by way of example in the figures of the accompanying drawings, in which like references indicate similar elements.

DETAILED DESCRIPTION

Figure 1:
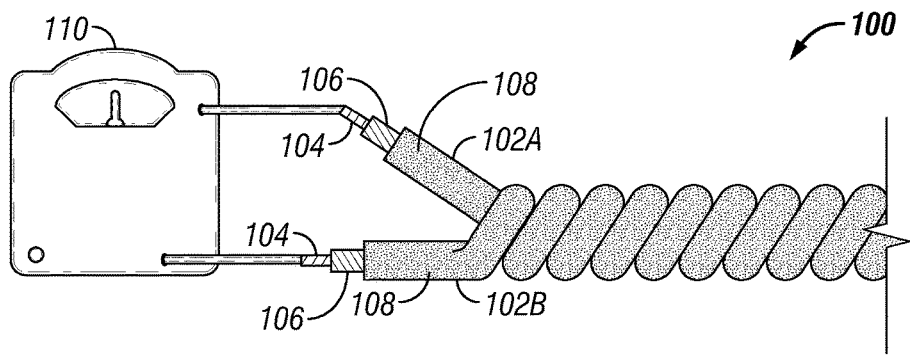
FIG. 1 is a diagram illustrating a side view of an embodiment of a leakage sensor assembly.

The present disclosure can be better understood by the following discussion of the manufacture and use of certain embodiments. In this description, references to "an embodiment," "one embodiment," "an implementation," or the like, mean that the particular feature, function, structure or characteristic being described is included in at least one embodiment of the technique introduced here. Occurrences of such phrases in this specification do not necessarily all refer to the same embodiment. On the other hand, the embodiments referred to also are not necessarily mutually exclusive. Like reference numerals are used to describe like parts in all figures of the drawings.

FIG. 1 is a diagram illustrating an embodiment of a leakage sensor cable assembly. A leakage sensor cable 100 comprises a first sensor cord 102a and a second sensor cord 102b. Each sensor cord 102 comprises at least three layers in the form of at least a conductive wire 104, a conductive coating layer 106, and a permeable shell 108. The conductive coating layer 106 is formed around the conductor wire 104. The water-permeable shell 108 is in turn formed around the conductive coating layer 106. The leakage sensor cable 100 is connected to an electronic indicator 110 that has at least the basic functionality of a resistance meter and is equipped with a positive terminal (not shown) and a negative terminal (not shown). The first sensor cord 102a is connected to a positive terminal and the second sensor cord 102b is connected to a negative terminal.

The first sensor cord 102a and the second sensor cord 102b are braided together by twisting them together along their lengths to form the leakage sensor cable 100. The manner in which the first sensor cord 102a and the second sensor cord 102b are braided together may vary and are not limited to that of a simple braid pattern where the first sensor cord 102a and the second sensor cord 102b are simply twisted together. Various braiding methods can be applied to tie together the first sensor cord 102a and the second sensor cord 102b.

The ends of the first sensor cord 102a and the second sensor cord 102b are connected to the electronic indicator 110 made as a resistance (or voltage) meter on one side, and on the other side, are capped with electrically insulating blanking plugs (not shown). The electrically insulating blanking plugs protect the measuring circuit against short-circuit.

The permeable shell 108 is a capillary-porous material capable of absorbing and diffusing a fluid (such as water) when the fluid comes into contact with the outer surface of the permeable shell 108. The fluid is absorbed into the permeable shell 108 through a capillary mechanism. The conductive fluid will then diffuse inwards in the direction of the conductive wire 104. Eventually the water reaches the conductive coating layer 106 and creates a conductive bridge between the conductive wire 104a and the conductive wire 104b. Consequently, continuously measured electrical resistance between the two conductive wires 104a and 104b changes and the mere fact that water is present somewhere in the length of the leakage sensor cable 100 is determined. Because the resistance value per unit length of the conductor wires 104a and 104b is known, the point of leakage where water (or some other conductive fluid) has formed a conductive bridge between the two conductor wires 104a and 104b can also be determined based on calculations. In the leakage sensor cable 100, the point of leakage is detected using the time-domain reflectometry method or the loop test method, which are both methods known in the art.

The conductive coating layer 106 is made up of a conductive polymer pound. The conductive polymer compound has a surface resistance Rs in the range of 1 to 103 Ohms and plastic elongation at break of 100% or more (could be verified via plastic test ASTM D638). Also, its Melt Flow Index (MFI) should not be more than 1.5 grams flowing in 10 minutes and the polymer can be applied to the conductive wire 104 by extrusion coating. This allows the conductive polymer compound 106 to be flexible but still strong after it is applied to the conductive wire 104. The conductive polymer compound may be comprised of polyolefin and carbon soot in a ratio of 4:1 to a ratio of 1:3. When the surface resistance Rs of the conductive coating layer 106 is too high, the complexity of the equipment required to detect conductivity increases. If elongation at break is less than 100% and MFI is more than 1.5 grams flowing in 10 minutes—the leakage sensor cable 100 will be lacking the required flexibility and strength creating the risk of breaking. As such, during manufacturing, the composition of e.g. polyolefin and carbon soot used to formulate the conductive polymer compound must be kept in a ratio of 4:1 to a ratio of 1:3 so the surface resistance of the conductive coating layer 106 can achieve a value between the range of 1 to 103 Ohms. Using a composition of polyolefin and carbon soot to formulate the conductive polymer compound allows the conductive coating layer 106 to be formed by extrusion coating.

By braiding the first sensor cord 102a and the second sensor cord 102b together, the surface area of the first permeable shell 108a and the second permeable shell 108b available for water leakage detection is increased for a given length of the leakage sensor cable 100 as compared to when the first sensor cord 102a and the second sensor cord 102b are simply arranged side-by-side. This increases the leakage sensor cable's 100 sensitivity to water. Braiding of the first sensor cord 102a and the second sensor cord 102b together can be used as an option to adjust the sensing sensitivity of the leakage sensor cable 100.

The sensor cord 102 is constructed such that its cross-sectional diameter ranges from 0.9 millimeters (mm) to 13 mm. The thickness of the conductive wire 104 can range from 0.2 mm to 5 mm. The thickness of the conductive coating layer 106 can range from 0.5 mm to 5 mm. The thickness of the permeable shell 108 can range from 0.2 mm to 3 mm. In one embodiment, the sensor cord can have a total cross-sectional diameter of 0.9 mm where the conductive wire 104, the conductive coating layer 106, and the permeable shell 108 are 0.2 mm, 0.5 mm, and 0.2 mm respectively. In another embodiment, the sensor cord can have a total cross-sectional diameter of 13 mm where the conductive wire 104, the conductive coating layer 106, and the permeable shell 108 are 5 mm, 5 mm, and 3 mm respectively. In yet another embodiment, the conductive wire 104, the conductive coating layer 106, and the permeable shell 108 are 2 mm, 2 mm and 1 mm respectively. The thickness of the three layers can be adjusted in accordance to meet a particular manufacturing cost. The thickness can also be adjusted to suit the surface or environment in which water detection is to be performed.

One characteristic of the permeable shell 108 is its porosity, which is the rate at which water molecules diffuse through the capillary porous material. The porosity of the capillary porous material is usually measured at a scale of 0% to 100% (or a value between 0 to 1). The required porosity is between a range of 0.2 to 0.8.

Figure 2:
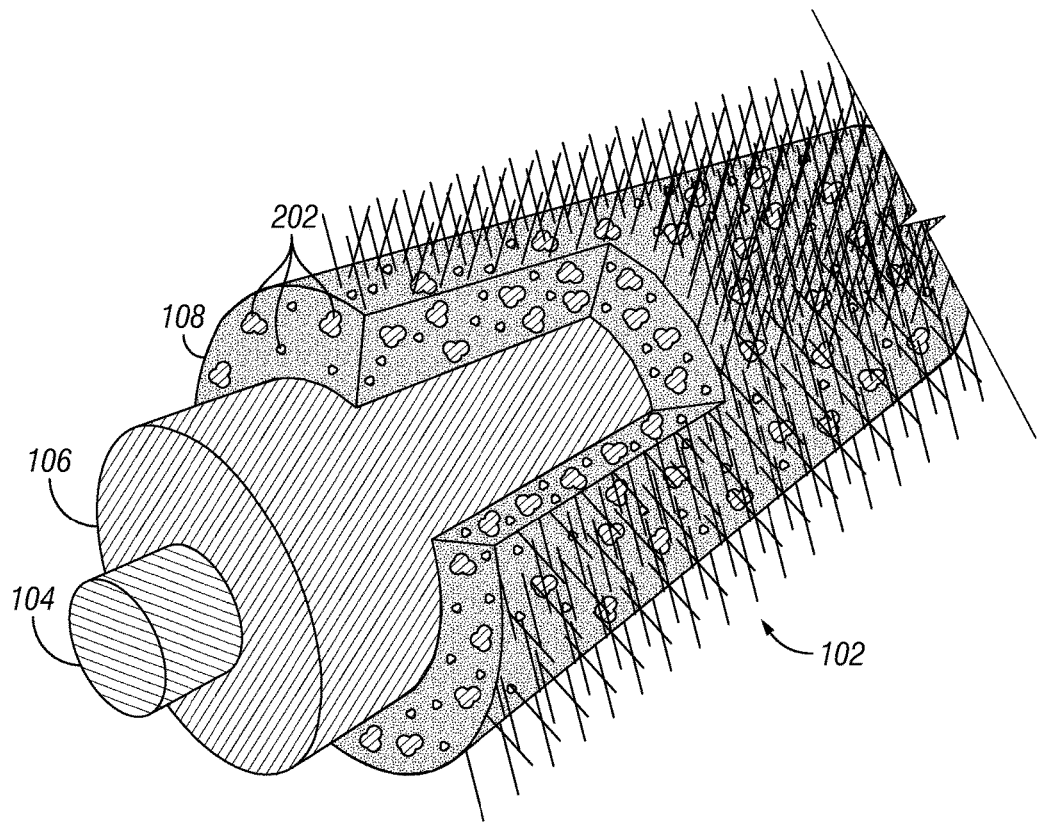
FIG. 2 is a diagram illustrating a partial perspective view of an embodiment of a leakage sensor cable with impregnated electrolyte particles.

FIG. 2 is a diagram illustrating a partial perspective view of an embodiment of a leakage sensor cable with impregnated electrolyte particles. The capillary-porous material used to form the permeable shell 108 can be organic or an inorganic nature (non-polymeric). Twisted fiber glass filament (or fiberglass roving) made from silicon dioxide ($SiO_2$) or aluminum oxide ($Al_2O_3$) are examples of the inorganic capillary-porous materials used to form the permeable shell 108. This type of capillary porous material has a complex and porous structure. For this type of capillary-porous material to transition from a dry dielectric state to a conductive state, much less water is required as compared to for example a mesh of plastic strands. The capillary porous material of the permeable shell 108 has nappy (needle-like) strands 112 extending from its surface. The large numbers of nappy strands 112 facilitate the condensation of vapor molecules on the tips of the nappy strands 112. The water molecules are then rapidly absorbed deeper into the permeable shell 108. The capillary-porous material provides fluid penetration and also serves as a fire-retardant, protecting the cable against flames in the event of a fire. Twisted fiber glass filament is also a more cost-effective material as compared to materials such as copper. A permeable shell 108 made of twisted fiber glass filament also provides other additional characteristics such as better chemical resistance. Using a twisted fiber-glass filament also provides better absorption characteristics as opposed to porous polymers. However, the permeable shell 108 may be made of polymer where narrow polymer threads are braided together creating a tourniquet/wisp. Other examples include basalt, cotton, linen and synthetics etc.

The permeable shell 108 may be impregnated with dried electrolyte particles 202 of an acid, an alkali, or a salt such as sodium-chloride. The electrolyte particles of any compound that can convert water into an electrolyte solution with an electrical resistance lower than that of the water can be used. Therefore the dried electrolyte particles are not limited to alkalis or surfactants. During manufacturing, the permeable shell 108 is soaked in a liquid electrolyte solution containing electrolyte particles dissolved within. Particles of the dry substance will become embedded (impregnated) on the surface and throughout the inside of the permeable shell 108. The water permeable shell 108 is comprised of numerous microscopic capillaries (not shown). These capillaries generally run tangentially from the outside surface of the permeable shell 108 inwards towards the conductive coating layer 106 but also run parallel to the surface. The capillaries crisscross the interior of the permeable shell 108. When the permeable shell 108 is soaked in the liquid electrolyte solution containing electrolyte parties dissolved within during manufacturing, the electrolyte particles enter the capillaries. When the permeable shell 108 dries, the electrolyte particles 202 remain adhered to inner walls of the capillaries.

When the permeable shell 108 comes into contact with water or another conductive fluid, the dried electrolyte particles 202 will revert back into a liquid electrolyte, thereby enhancing the electrical conductivity of the penetrating conductive fluid.

When chemically clean and fully deionized water comes into contact with the permeable shell 108, the dried electrolyte particles 202 dissolve into the chemically clean and fully deionized water. The deionized water is enriched with ions and becomes conductive. Now ionized, the previously deionized water is able to conduct electricity and create a short circuit. Thus, the invention makes it possible to detect leaks of all types of water, with virtually any electrical resistance (with an electrical resistance of up to 18 megohms-cm [1], the degree of purification—99.99999991%.) The embedding of electrolyte particles within the permeable shells 108 along the inner walls of the numerous capillaries not only increases the sensitivity and accuracy of the leakage sensor cable 100 and enables the detection of water in various states, including the detection of water vapor and steam, but also enhances the conductivity of deionized water so it is detectable.

Figure 3:
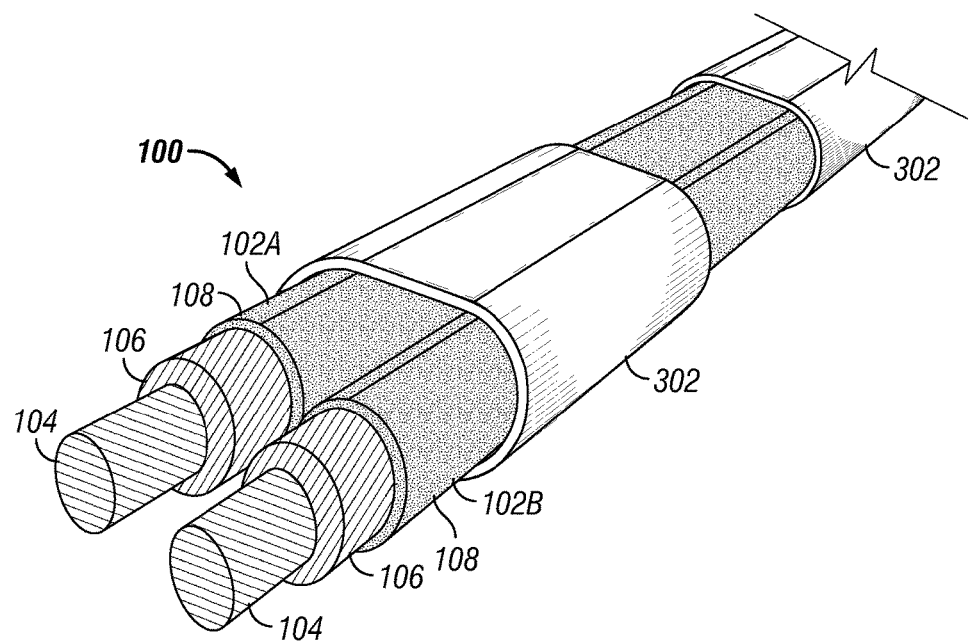
FIG. 3 is a diagram illustrating a partial perspective view of an embodiment of a leakage sensor cable.

FIG. 3 is a diagram illustrating an embodiment of the leakage sensor cable with an impermeable layer 302. The impermeable layer 302 does not allow water or any other fluid to pass through. In order to prevent accidental or faulty detections along portions of the leakage sensor cable 100 for example where there may be water present around the sensor cable but is not necessarily the result of a leak, the leakage sensor cable 100 can be shielded in some areas with the impermeable layer 302. The impermeable layer 302 can be configured to encapsulate the leakage sensor cable 100 in a single large section or in multiple smaller sections depending on the need for water leakage detection along that particular portion of the leakage sensor cable 100. In this embodiment, although the first sensor cord 102a and the second sensor cord 102b are arranged side-by-side together, they can optionally be braided together before being encapsulated by the impermeable layer 302.

Figure 4:
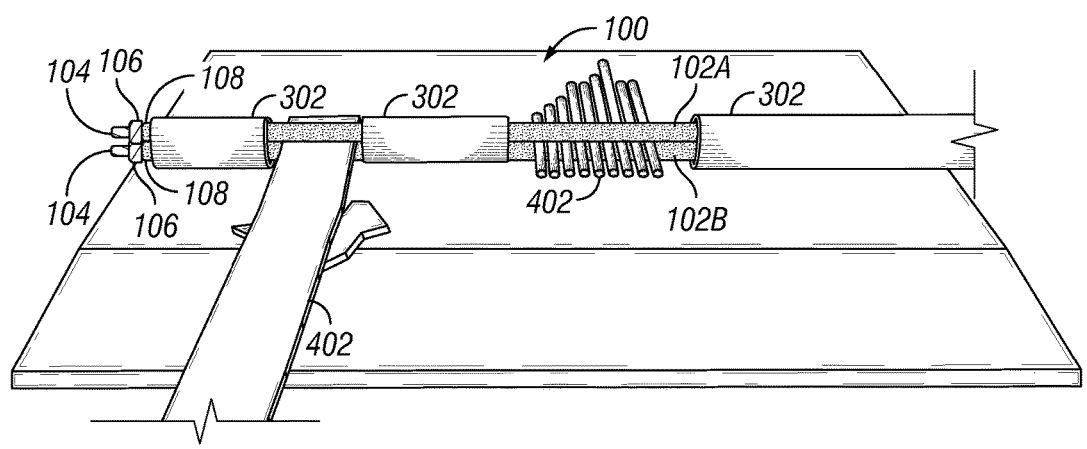
FIG. 4 is a diagram illustrating a side view of an embodiment of a leakage sensor cable when mounted to a surface.

FIG. 4 is a diagram illustrating an embodiment of the leakage sensor cable 100 with taps 402 attached. Taps 402 are extensions attached to the leakage sensor cable 100 to extend its reach. The leakage sensor cable 100 can be easily and affordably mounted to a variety of surfaces. The leakage sensor cable's 100 control zone can be substantially increased by adding taps 402 to the leakage sensor cable 100. The taps 402 can be made of the same capillary-porous material as the permeable shell 108. The taps 402 may be attached by inserting them between the first sensor cord 102a and the second sensor cord 102b. When the taps 402 come into contact with water or a conductive fluid, the water diffuses through the taps until they reach the leakage sensor cable 100. By only using the water permeable taps 402, the control zone of a water leakage assembly can be increased using less lengths of the leakage sensor cable 100 that are more costly than the taps 402. In this embodiment the taps 402 are shown as straight strips, however, they are not limited to a straight shape and may be curved or cut to other shapes to suit the particular environment in which the leakage sensor cable 100 is applied.

Using the taps 402 the leakage sensor cable 100 can be mounted in premises of different intricate shapes. The leakage sensor cable 100 alone can be mounted on ceilings, floors, walls, both in horizontal and in vertical positions based on the expected direction of a potential water leak or drip. The leakage sensor cable 100 can even be mounted on an inverted sloping surface that is not flat but due to the surface tension between water and that particular surface, the water is flowing down its side. The leakage sensor cable 100 can also be made to conform to the curvature of the inverted sloping surface. The taps 402 are then used to access hard-to-reach places that are lateral to the leakage sensor cable 100. When crossing locations where the presence of water is normal and water detection is not necessary or desired, the leakage sensor cable 100 is covered with the impermeable layer 302.

Figure 5:
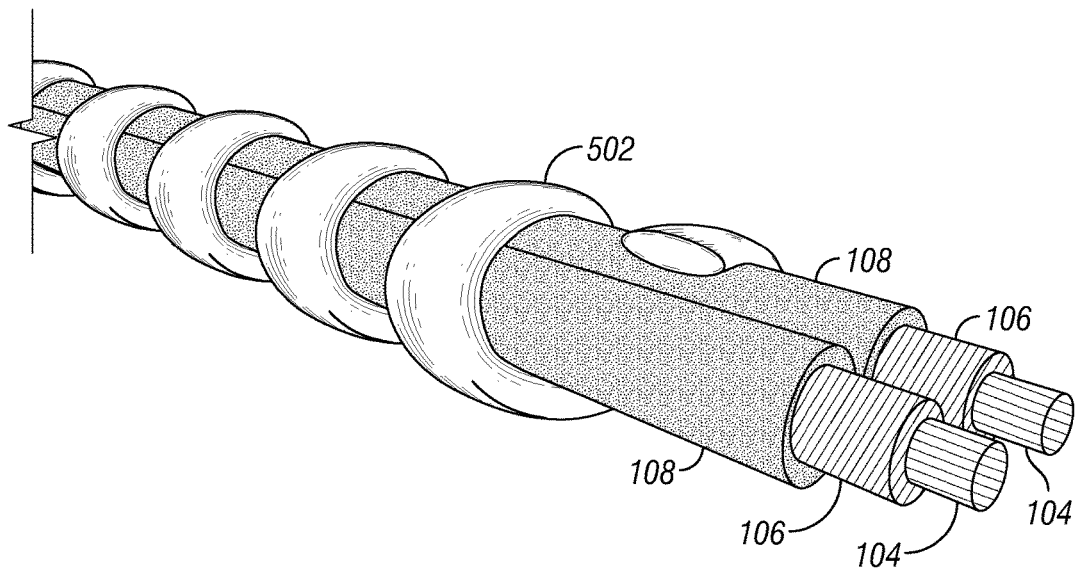
FIG. 5 is a diagram illustrating a partial perspective view of an embodiment of a leakage sensor cable.

FIG. 5 illustrates an embodiment of the leakage sensor cable 100 secured with a fastening thread 502. The first sensor cord 102a and the second sensor cord 102b of the leakage sensor cable 100 can be kept together throughout its length using a fastening thread 502. The fastening thread 502 is non-conductive and does not obstruct the functioning of the leakage sensor cable 100. It simplifies the manufacture of the leakage sensor cable 100 so twists in the coating layers will be unnecessary. The fastening thread 502 can be made of glass fiber that is 0.2 millimeters in diameter with a winding pitch of 10 millimeters. This simplifies the manufacturing process of the leakage sensor cable without causing sensitivity deterioration through the use of a large diameter thread. The fastening thread 502 may also be made of a non-conductive material such as basalt, synthetic, cotton, or linen etc.

Figure 6:
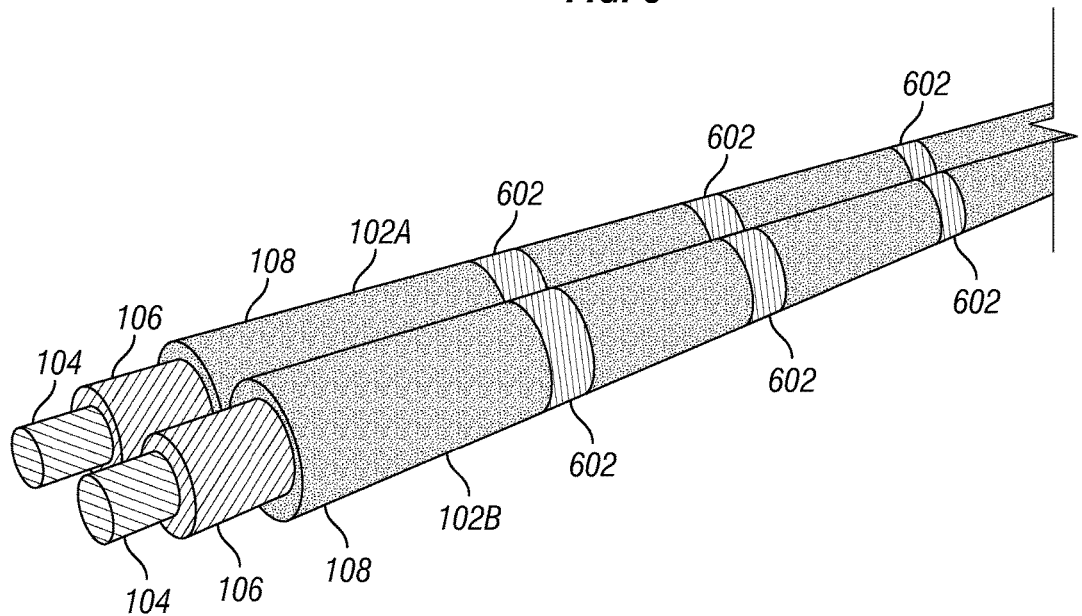
FIG. 6 is a diagram illustrating a partial perspective view of an embodiment of a leakage sensor cable.

FIG. 6 illustrates an embodiment of the leakage sensor cable 100 where portions of the permeable shell 108 encasing the conductive coating layer 106 are replaced with inserts 602. Interspersed between lateral sections of the permeable shell 108 are inserts 602, which are made of a water impermeable and electrically insulated material. The inserts 602 provide another improvement to the functionality of the leakage sensor cable 100. In this case, the water (or conductive fluid) will not be able to diffuse laterally within the permeable shell 108 of the leakage sensor cable 100 for an unlimited distance. Water entering a section of the permeable shell 108 bounded on each side by inserts 602 will only be able to diffuse as far as that section of the permeable shell 108. This increases the sensor's accuracy as to the detection of the precise leakage point. Regardless of how the leakage sensor cable 100 is mounted, the embodiment containing inserts 602 can be used to limit the indefinite lateral diffusion of water within the length of permeable shell 108. This way, only the contact of water with a particular section of the leakage sensor cable 100 will lead to sensor actuation, allowing the detection of fluid leakage on any surface to be narrowed to a more precise location.

Overall, the disclosed leakage sensor cable 100 achieves the desired technical result including increased sensitivity while simultaneously achieving an increased scope of use, greater accuracy of detection of the leakage location, and a simplified manufacturing process.

Note that any and all of the embodiments described above can be combined with each other, except to the extent that it may be stated otherwise above or to the extent that any such embodiments might be mutually exclusive in function and/or structure.

Other alterations and modifications of the disclosure will likewise become apparent to those of ordinary skill in the art upon reading the present disclosure, and it is intended that the scope of the disclosure made herein be limited only by the broadest interpretation of the appended claims to which the inventor is legally entitled.

Although the present disclosure has been described with reference to specific exemplary embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. Unless otherwise specifically stated, the terms and expressions have been used herein as terms of description and not terms of limitation. There is no intention to use the terms or expressions to exclude any equivalent of features shown and described or portions thereof and this disclosure should be defined in accordance with the claims that follow.

REFERENCE SIGNS LIST

The following items are denoted in the drawing:
100—leakage sensor cable
102—sensor cord
104—conductive wire;
106—conductive coating layer;
108—permeable shell;
110—electronic indicator made as a resistance (or voltage) meter;
302—impermeable layer;
402—taps;
502—fastening thread.
602—inserts

What is claimed is:

1. A device comprising:
a first conductive wire and a second conductive wire;
a first conductive coating layer formed around the first conductive wire;
a second conductive coating layer formed around the second conductive wire;
a first permeable shell formed around the first conductive coating layer to form a first sensor cord;
a second permeable shell formed around the second conductive coating layer to form a second sensor cord; and
wherein the first sensor cord and the second sensor cord are arranged together along their lengths to form a leakage sensor cable;
wherein the first and second permeable shells are a capillary-porous material capable of absorbing and diffusing a fluid when the fluid comes into contact with the first and second permeable shells;
wherein the first and second permeable shells have a plurality of nappy strands extending outwards from a surface of the permeable shell;
a plurality of taps made of the capillary porous material attached to the leakage sensor cable and extending away from the leakage sensor cable; and
electrolyte particles impregnated within the first permeable shell and the second permeable shell to enhance the conductivity of the fluid.

2. The device in claim 1, wherein the electrolyte particles are a salt.

3. The device in claim 1, wherein the first and second conductive coating layers are made of a conductive polymer compound applied by extrusion coating.

4. The device in claim 1, further comprising a plurality of impermeable inserts formed around the first conductive coating layer and the second conductive coating layer immediately adjacent to the first permeable shell and second permeable shell.

5. The device in claim 1, further comprising a fastening thread coiled around the leakage sensor cable.

6. The device in claim 5, wherein the fastening thread is made of a non-conductive material.

7. The device in claim 1, further comprising a water impermeable layer configurable to form a single water impermeable section or a plurality of water impermeable sections.

8. A device comprising:
a first conductive wire and a second conductive wire;
a first conductive coating layer formed around the first conductive wire;
a second conductive coating layer formed around the second conductive wire;
a first permeable shell formed around the first conductive coating layer to form a first sensor cord;
a second permeable shell formed around the second conductive coating layer to form a second sensor cord; and
wherein the first sensor cord and the second sensor cord are arranged side-by-side along their lengths to form a leakage sensor cable;
wherein the first and second permeable shells are a capillary-porous material capable of absorbing and diffusing a fluid when the fluid comes into contact with the first and second permeable shells;
wherein the first and second permeable shells have a plurality of nappy strands extending outwards from a surface of the permeable shell;
a plurality of taps made of the capillary porous material attached to the leakage sensor cable and extending away from the leakage sensor cable; and
electrolyte particles impregnated within the first permeable shell and the second permeable shell to enhance the conductivity of the fluid.

9. A method of detecting a fluid comprising:
forming a first conductive coating layer around a first conductive wire;
forming a first permeable shell around the first conductive coating layer to create a first sensor cord;
forming a second conductive coating layer around a second conductive wire;
forming a second permeable shell around the second conductive coating layer to create a second sensor cord; and
arranging the first sensor cord and the second sensor cord together along their lengths to form a leakage sensor cable;
forming the first and second permeable shells with a capillary-porous material capable of absorbing and diffusing a fluid when the fluid comes into contact with the first and second permeable shells;
forming the first and second permeable shells with a plurality of nappy strands extending outwards from a surface of the permeable shell;
forming a plurality of taps made of the capillary porous material attached to the leakage sensor cable and extending away from the leakage sensor cable;
impregnating within the first permeable shell and the second permeable shell electrolyte particles to enhance the conductivity of the fluid;
dissolving electrolyte particles into a fluid that enters the first permeable shell and the second permeable shell to enhance the conductivity of the fluid; and
conducting an electrical current from the first conductive wire to the second conductive wire through the fluid.

* * * * *